United States Patent [19]

Young et al.

[11] Patent Number: 5,663,169

[45] Date of Patent: Sep. 2, 1997

[54] BENZOXAZINONES AS INHIBITORS OF HIV REVERSE TRANSCRIPTASE

[75] Inventors: Steven D. Young; Linda S. Payne, both of Lansdale; Susan F. Britcher, Norristown; Lekhanh O. Tran, West Chester; William C. Lumma, Jr., Pennsburg, all of Pa.

[73] Assignee: Merck & Co., Inc., Rahway, N.J.

[21] Appl. No.: 458,528

[22] Filed: Jun. 2, 1995

Related U.S. Application Data

[60] Division of Ser. No. 188,005, Jan. 28, 1994, which is a continuation-in-part of Ser. No. 54,805, Apr. 27, 1993, abandoned, which is a continuation-in-part of Ser. No. 926,607, Aug. 7, 1992, abandoned.

[51] Int. Cl.$^6$ .............................................. A61K 31/535
[52] U.S. Cl. ................................................ 514/230.5
[58] Field of Search ...................................... 514/230.5

[56] References Cited

U.S. PATENT DOCUMENTS

| | | | |
|---|---|---|---|
| 3,526,621 | 9/1970 | Bernardi et al. | 260/244 |
| 3,682,933 | 8/1972 | Engel | 260/244 |
| 4,313,873 | 2/1982 | Lim | 260/18 TN |
| 4,857,511 | 8/1989 | Rideout et al. | 514/50 |
| 5,179,093 | 1/1993 | Afonso et al. | 514/235.2 |
| 5,434,152 | 7/1995 | Huffman et al. | 514/234.5 |

FOREIGN PATENT DOCUMENTS

| | | | |
|---|---|---|---|
| 0 093 922 | 4/1983 | European Pat. Off. | |
| 394 553 A2 | 11/1989 | European Pat. Off. | A61K 31/47 |
| 384 552 A1 | 2/1990 | European Pat. Off. | C07D 487/06 |
| 491218 A1 | 12/1991 | European Pat. Off. | C07D 403/04 |
| 1135899 | 7/1967 | United Kingdom | C07D 87/00 |
| WO 91/09849 | 7/1991 | WIPO | A61K 31/40 |
| WO 91/18591 | 12/1991 | WIPO | A61K 31/00 |
| WO 92/00979 | 1/1992 | WIPO | A61K 31/58 |
| WO 92/04328 | 3/1992 | WIPO | C07D 215/56 |
| WO 92/16508 | 10/1992 | WIPO | |

OTHER PUBLICATIONS

Young et al 120 CA: 270428c 1994.
"AIDS, The unanswered questions", Science, vol. 260, pp. 1253–1293, (May, 1993).
Young, et al., "Diazines", Chem. Ab., vol. 120, 270423, p. 1074, (1994).
Mayers, D.,"A double blind pilot to evaluate the antiviral activity, tolerability & pharmacokinetics of DMP 266 alone & in combination with indinavir", Abstract No. LB8a, 36th Interscience Conference on Antimicrobial Agents & Chemotherapy, (1996).
Young, L. S., et al., "Activity of ciprofloxacin and other fluorinated quinolones against mycobacteria", Amer. J. of Medicine, vol. 82(Suppl. 4a), pp. 23–26, (1987).
Bernardi, L., et al., "Central depressant properties of 3,1-benzoxazine derivatives", Experientia, vol. 25(8), pp. 787–788, (1969).
Carretero, J.C., et al., "A practical route to C–8 substituted fluoroquinolones", Tetrahedron, vol. 48(35), pp. 7373–7382, (1992).
Rastogi, N., et al., "Enhancement of drug susceptibility of Mycobacterium avium by inhibitors of cell envelope synthesis", Antimicrobial Agents & Chemotherapy, vol. 34(5), pp. 759–764, (1990).
Kukla, M.J., et al., "Synthesis and Anti-HIV-1 activity of 4,5,6,7-tetrahydro-5-methylimidazo[4,5,1-jk][1,4] benzodiazepin-2(1H)-one (TIBO) derivatives", J. of Medicinal Chem., vol. 34(11), pp. 3187–3197 (1981).
Gioia, B., et al., "Identification of the metabolites of brofoxine in rate urine. Mass spectrometry studies", Adv. Mass. Spectrum, 7B, pp. 1622–1627, (1978).
Banerjee, D.K., et al., "Evaluation of the activity of a number of antimicrobial agents against mycobacteria within mouse macrophages by a radiometric method", J. of Antimicrobial Chemotherapy, vol. 31, pp. 289–302 (1993).
Hartman, R.J., et al., "Effects of brofoxine, a new anxiolytic on experimentally induced conflict in rats", Proc. West. Pharmacol, Soc., vol. 21, pp. 51–55 (1978).
Nozaki-Renard, J., et al., "A fluoroquinolone (DR-3355) protects human lymphocyte cell lines from HIV-1-induced cytotoxicity", AIDS, (London), vol. 4(12), pp. 1283–1286, (1990).
Menozzi, M., et al., "Interaction of brofoxine with serum proteins", Farmaco, Ed. Sci., vol. 35(1), pp. 79–88 (1980).
Lewin, C.S., et al., "Susceptibility of bacterial isolates from AIDS patients to six fluoroquinolones", J. Pharm., & Pharmacol., vol. 42(11), pp. 808–809, (1990).
Lewin, C.S., et al., "Antibacterial activity of fluoroquinolones in combination with zidovudine", J. Med. Microbiol., vol. 33, pp. 127–131 (1990).
Nozaki-Renard, J., et al., "Fluoroquinolones protect the human lymphocyte CEM cell line from HIV-1-mediated cytotoxicity", Cell Structure & Function, vol. 15(5), pp. 295–299 (1990).
Nordmann, P., et al., "In-vitro antimicrobial susceptibility of Rhodococcus equi", J. of Antimicro. Chemotherapy, vol. 29, pp. 383–393 (1992).

Primary Examiner—Russell Travers
Attorney, Agent, or Firm—Valerie J. Camara; Mark R. Daniel

[57] ABSTRACT

Certain benzoxazinones are useful in the inhibition of HIV reverse transcriptase (including its resistant varieties), the prevention or treatment of infection by HIV and the treatment of AIDS, either as compounds, pharmaceutically acceptable saks, pharmaceutical composition ingredients, whether or not in combination with other antivirals, immunomodulators, antibiotics or vaccines. Methods of treating AIDS and methods of preventing or treating infection by HIV are also described.

4 Claims, No Drawings

BENZOXAZINONES AS INHIBITORS OF HIV REVERSE TRANSCRIPTASE

This is a division of application Ser. No. 08/188,005, filed Jan. 28, 1994, which is a continuation-in-part of Merck Case 18793IA, filed Apr. 27, 1993, U.S. Ser. No. 08/054,805, which is a continuation-in-part of Merck Case 18793, filed Aug. 7, 1992, U.S. Ser. No. 07/926,607, both now abandoned.

BACKGROUND OF THE INVENTION

This case is related to Merck Cases 18429, Ser. No. 07/746,445, filed Aug. 16, 1991, now abandoned, 18429IA, Ser. No. 07/880,121, filed Aug. 7, 1992, now abandoned, and 18727.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

Applicants demonstrate that the compounds of this invention are inhibitors of HIV reverse transcriptase. The particular advantages of the present compounds are their demonstrated inhibition of resistant HIV reverse transcriptase.

BRIEF DESCRIPTION OF THE INVENTION

Compounds of formula I, as herein defined, are disclosed. These compounds are useful in the inhibition of HIV reverse transcriptase (and its resistant varieties), the prevention of infection by HIV, the treatment of infection by HIV and in the treatment of AIDS and/or ARC, either as compounds, pharmaceutically acceptable salts (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with compounds of formula I, combinations thereof, or pharmaceutically acceptable salts thereof, in the inhibition of HIV reverse transcriptase and its resistant varieties, the prevention or treatment of infection by HIV and in the treatment of the resulting acquired immune deficiency syndrome (AIDS). Compounds of formula I are defined as follows:

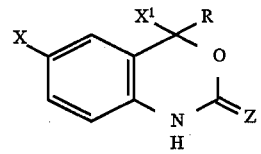

wherein:
X is halo,
$X^1$ is trihalomethyl, or pentahaloethyl;
Z is O;
R is
(a) $C_{1-8}$ alkyl, unsubstituted or substituted with A, and A is halo, $C_{3-6}$ cycloalkyl, CN, hydroxy, $C_{1-4}$ alkoxy, $C_{2-4}$ alkynyl-$C_{1-4}$ alkoxy, aryloxy, $C_{1-4}$ alkylcarbonyl, nitro, di($C_{1-2}$alkyl)amino, $C_{1-4}$ alkylamino-$C_{1-2}$ alkyl, heterocycle, or arylthio;
(b) $C_{2-4}$ alkenyl, unsubstituted or substituted with
(i) A, or
(ii) aryl, unsubstituted or substituted with A;
(c) $C_{2-5}$ alkynyl, unsubstituted or substituted with
(i) A, or
(ii) aryl, unsubstituted or substituted with A; or
(d) $C_{3-4}$ cycloalkyl, unsubstituted or substituted with
(i) A, or
(ii) aryl, unsubstituted or substituted with A,
or pharmaceutically acceptable salt thereof.

This invention also encompasses a pharmaceutical composition useful for inhibiting HIV reverse transcription, comprising an effective amount of a compound of Formula II,

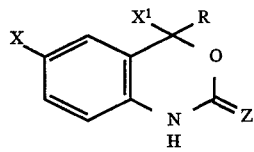

and a pharmaceutically acceptable carrier, wherein
X is halo;
$X^1$ is trihalomethyl; pentahaloethyl; $C_{2-5}$ alkyl;
$C_{2-5}$ alkynyl;
$C_{3-5}$ cycloalky; or aryl;
Z is O or S;
R is
(a) $C_{1-8}$ alkyl, unsubstituted or substituted with A, and A is halo, $C_{3-6}$ cycloalkyl, CN,hydroxy, $C_{1-4}$ alkoxy, $C_{2-4}$ alkynyl-$C_{1-4}$ alkoxy, aryloxy, $C_{1-4}$ alkylcarbonyl, nitro, di($C_{1-2}$ alkyl)amino, $C_{1-4}$ alkylamino-$C_{1-2}$ alkyl, heterocycle, or arylthio;
(b) $C_{2-4}$ alkenyl, unsubstimted or substituted with
(i) A, or
(ii) aryl, unsubstituted or substituted with A;
(c) $C_{2-5}$ alkynyl, unsubstituted or substituted with
(i) A, or
(ii) aryl, unsubstituted or substituted with A; or (d) $C_{3-4}$ cycloalkyl, unsubstituted or substituted with
(i) A, or
(ii) aryl, unsubstituted or substituted with A,
or pharmaceutically acceptable salt thereof.

Preferred compounds include Compounds 37.2, 4, 2, 5 and 24 of Table I below, in order of descending degree of preference. These compounds have the following structure:

Compound 37.2:

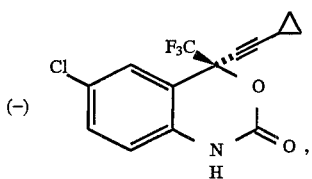

(−) 6-Chloro-4-cyclopropylethynyl-4-trifluoromethyl-1,4-dihydro-2H-3,1-benzoxazin-2-one, the most preferred;

Compound 4:

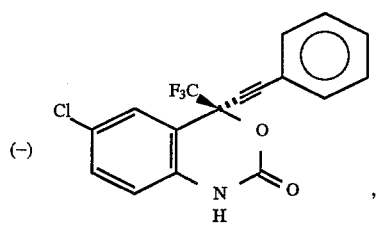

(−) 6-chloro-4-phenylethynyl-4-trifluoromethyl-1,4-dihydro-2H-3,1-benzoxazin-2-one;

Compound 2:

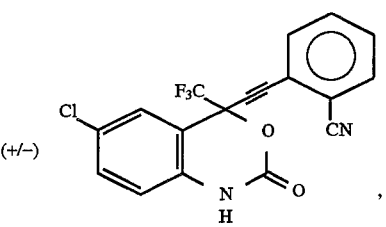

(+/−) 6-chloro-4-(2-cyanophenyl)ethynyl-4-(1,1,1-trifluoromethyl)-1,4-dihydro-2H-3,1-benzoxazin-2-one;

Compound 5:

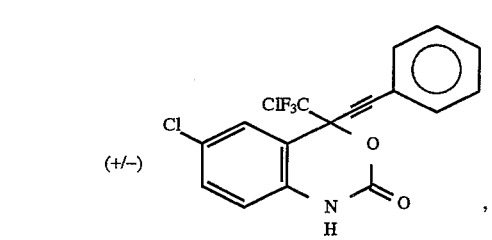

(+/−) 4-(1-chloro-1,1-difluoromethyl)-4-(2-phenyl-ethynyl)-6-chloro-1,4-dihydro-2H-3,1-benzoxazin-2-one;

Compound 24:

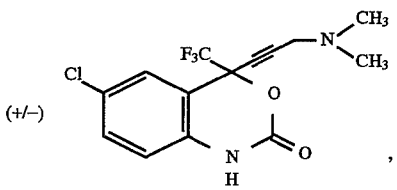

(+/−) 4-(2-[dimethylaminomethyl]ethynyl)-4-trifluoromethyl-6-chloro-1,4-dihydro-2H-3,1benzoxazin-2-one;

or a pharmaceutically acceptable salt thereof.

The compounds of the present invention are specifically illustrated in Tables I and II below:

TABLE I

| Compound | R | $X^1$ | MP(°C.) | $IC^*_{50}$ wt | $IC^*_{50}$ dm | $CIC^*_{95}$ |
|---|---|---|---|---|---|---|
| 1 | *—≡—⌬—OCH₃ | —CF₃ | 186–187.5 | 58 nM | 4100 nM | |
| 2 | *—≡—⌬—CN | —CF₃ | 245–246 | 25 | 480 | 6 nM |
| 3(+) | *—≡—⌬ | —CF₃ | 178–179 | 2900 | 37,000 | >200 |

TABLE I-continued
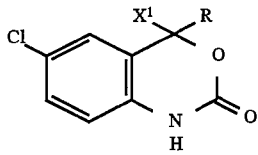
| Compound | R | X¹ | MP(°C.) | IC*$_{50}$ wt | IC*$_{50}$ dm | CIC*$_{95}$ |
|---|---|---|---|---|---|---|
| 4(−) | *−≡−phenyl | −CF$_3$ | " | 8.6 | 69 | 12 |
+measured in nM or nanomoles/liter.
| | | | | | | |
|---|---|---|---|---|---|---|
| 5 | *−≡−phenyl | −CF$_2$Cl | 154–155 | 12 nM | 350 nM | |
| 6 | *−≡−(2-NO$_2$-phenyl) | −CF$_3$ | 225–226 | 1,700 | 19,000 | |
| 7 | *−≡−N(pyrrolidine) | −CF$_3$ | 160–161 | 91 | 3,460 | |
| 8 | *−≡−(4-methylphenyl) | −CF$_3$ | 183–184 | 163 | 8,470 | |
| 9 | *−≡−(thiopyran) | −CF$_3$ | 168–171 | 83 nM | 210 nM | |
| 10 | *−≡−(3-O-phenyl) | −CF$_3$ | 159–160 | 18 | 390 | |
| 11 | *−≡−(2-OCH$_3$-phenyl) | −CF$_3$ | 185–186 | 16 | 270 | 6.0 nM |
| 12(+/−) | *−≡−phenyl | −CF$_3$ | 137–147 | 12 | 280 | 25 |
| 13 | CH$_3$O, H, *, CO$_2$CH$_3$ | −CF$_3$ | 157 | 390 nM | 10$^5$ nM | |
| 14 | *−−−Cl | −CF$_3$ | 174–176 | 130 | 65,000 | |
| 15 | *−−=  | −CF$_3$ | 165–166 | 29 | >10$^5$ | |

TABLE I-continued

Structure: 4-chloro-phenyl with $X^1$, R, and carbamate group (NH-C(=O)-O) forming a ring with the CR group.

| Compound | R | $X^1$ | MP(°C.) | $IC^*_{50}$ wt | $IC^*_{50}$ dm | $CIC^*_{95}$ |
|---|---|---|---|---|---|---|
| 16 | (oxazolidinone-CH₂-) | $-CF_3$ | 230–240 | 1900 | 1900 | 78,000 |
| 17 | propyl | $-CF_3$ | 132–133 | 2300 | >10⁵ | |
| 18 | HC≡C-CH₂-O- | $-CF_3$ | 148–149 | 15 nM | 2,650 nM | 50 nM |
| 19 | pentyl | $-CF_3$ | 136–137 | 24 | 25,000 | |
| 20 | phenyl | $-CF_3$ | 162–164 | 145 | 10⁵ | |
| 21 | -S-phenyl | $-CF_3$ | 145–146 | 860 | 125,000 | |
| 22 | -CH₂CH₂-phenyl | " | 150–151 | 55 | 3,650 | |
| 23 | -C≡CH | $-CF_3$ | 131–133 | 1300 nM> | 30,000 nM | |
| 24 | -C≡C-CH₂-N(CH₃)₂ | $-CF_3$ | 146.5–147.5 | 43 | 1950 | 100 |
| 25 | -CH=CH-CH₃ | $-CF_3$ | 122–124 | 220 | >10⁵ | |
| 26 | -C≡CH | $-CF_3$ | 224–225 | 0.24 | >10⁵ | |
| 27 | -C≡C-CH₂-OH | " | 203–204 | 550 | >10⁵ | |
| 28 | butyl | cyclopropyl | 118–120 | 307 nM | 114,250 nM | 1500 nM |
| 29 | -C≡CH | butyl | 166–168 | 1,900 | >10⁵ | |
| 30 | -C≡C-CH₂-O- | cyclopropyl | 100–101.5 | 410 | 3000 | |
| 31 | -C≡C-CH₂-N(CH₃)₂ | cyclopropyl | 140.5–141.5 | 410 | 4250 | |
| 32 | butyl | phenyl | 172–173 | 5400 | | |

TABLE I-continued

Structure: 4-chloro-2-(CR(X¹))-phenyl carbamate (N-H, C(=O)-O)

| Compound | R | X¹ | MP(°C.) | IC*₅₀ wt | IC*₅₀ dm | CIC*₉₅ |
|---|---|---|---|---|---|---|
| 33 | *-CH₂-CH₃ (ethyl) | *-phenyl | 277–278 | 300 nM | | |
| 34 | *-CH₂-CH₃ (ethyl) | *-CH₂-CH₃ (ethyl) | 125–126 | 16,500 | >300,000 nM | |
| 35 | *-C≡CH | *-phenyl | 184–185 | 650 | >300,000 | |
| 36 | *-CH₂-CH₃ | *-n-butyl | 151–152 | 52 | >300,000 | |
| 37 | *-n-propyl | *-t-butyl | 186–187 | 5,300 | >10⁵ | |
| 37.2(−) | *-C≡C-cyclopropyl | *-CF₃ | | 2 nM | 85⁺ nM | |

⁺other data on Compound 38 is provided in the Examples section.

TABLE II

Structure: 4-chloro-2-(CR(X¹))-phenyl thiocarbamate (N-H, C(=S)-S)

| Compound | R | X¹ | MP(°C.) | IC*₅₀ wt | IC*₅₀ dm | CIC*₉₅ |
|---|---|---|---|---|---|---|
| 38 | *-cyclopropyl | *-cyclopropyl | 177–179 | 136 nM | >300,000 nM | |
| 39 | *-cyclopropyl | *-isopropyl | 135–136 | 510 | >300,000 nM | |
| 40 | *-cyclopropyl | *-n-butyl | 125–126 | 48 | 29,000 | |
| 41 | *-ethyl | *-cyclopentyl | | 1400 nM | >300,000 nM | |
| 42 | *-n-propyl | *-phenyl | 218–220 | 1450 | | |
| 43 | *-n-propyl | *-phenyl | 187–188 | 610 | | |

TABLE II-continued

![structure with Cl-phenyl, X¹, R, NH-C(=S)-O group]

| Compound | R | X¹ | MP(°C.) | IC*₅₀ wt | IC*₅₀ dm | CIC*₉₅ |
|---|---|---|---|---|---|---|
| 44 | *—CH(CH₃)— (isopropyl *) | *—C₆H₅ (phenyl *) | 206–207 | 15 nM | >300,000 nM | 100 nM |
| 45 | *—CH(CH₃)— (isopropyl *) | *—CH(CH₃)— (isopropyl *) | 147–148 | 560 | >300,000 nM | |
| 46 | *—cyclopropyl | *—C₆H₅ (phenyl *) | 186–187 | 41 | >300,000 nM | |

The compounds of the present invention may have asymmetric centers and may occur, except when specifically noted, as racemates, racemic mixtures or as individual diastereomers, or enantiomers, with all isomeric forms being included in the present invention. The term (+/−) is intended to encompass (+) optical isomers or (−) optical isomers or mixtures thereof.

When any variable (e.g., R) occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms; "alkenyl" is intended to cover both branched- and straight chain alkyl groups with at least one carbon-carbon double bond; "alkynyl" is intended to cover both branched- and straight chain alkyl groups with at least one carbon-carbon triple bond. "Halogen" or "halo" as used herein, means fluoro, chloro, bromo and iodo.

As used herein, with exceptions as noted, "aryl" is intended to mean phenyl, naphthyl, tetrahydronaphthyl, biphenyl, phenanthryl, anthryl or acenaphthyl.

The term heterocycle or heterocyclic, as used herein except where noted, represents a stable 5- to 7-membered monocyclic or stable 8- to 11-membered bicyclic heterocyclic ring which is either saturated, partially unsaturated or unsaturated, and which consists of carbon atoms and from one to four heteroatoms selected from the group consisting of N, O and S, and wherein the nitrogen and sulfur heteroatoms may optionally be oxidized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, benzofuranyl, tetrahydropyranyl, thienyl, benzothienyl, thiamorpholinyl, thiamorpholinyl sulfoxide, thiamorpholinyl sulfone, and oxadiazolyl.

The compounds of the present invention can be synthesized by the following methods.

SCHEME I

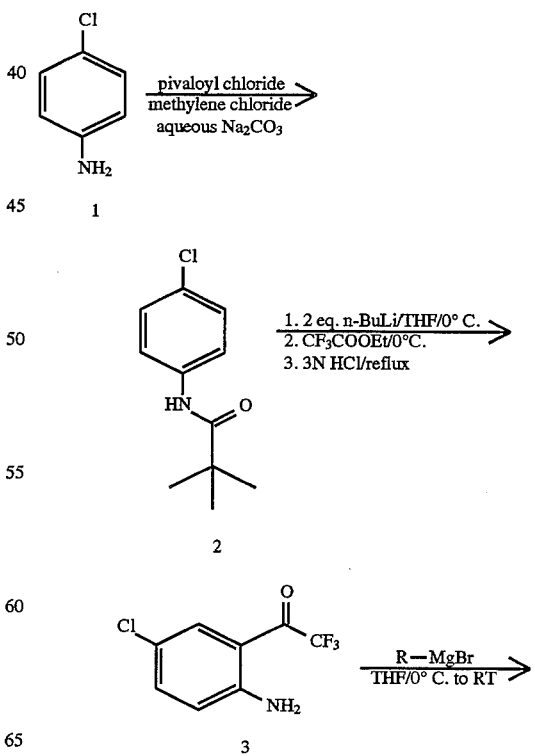

-continued
SCHEME I

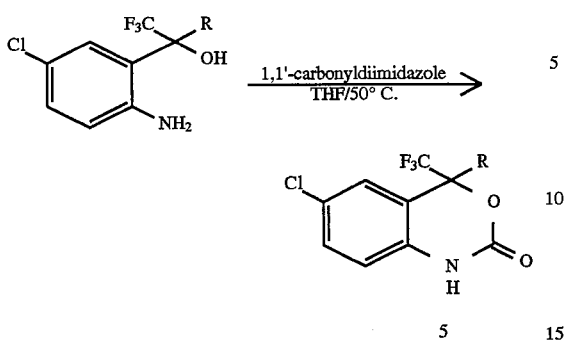

In the synthesis of the benzoxazines of the present invention, the general method typically involves cyclization on a benzene nucleus as a final step. See Scheme I. The amino group of parachloroaniline is first protected with, e.g. pivaloyl chloride, to give 2. Other less preferable amino protecting groups include t-butoxy-carbonyl, acetate or isovaleroyl groups. About 2 equivalents of an alkyllithium are then reacted with 2, preferably n-butyl lithium. No other organo metallic compounds are suitable for this metalation step. Subsequently, reaction with $CF_3COOEt$ followed by quenching gives 3.

The synthesis of the tertiary carbinol 4 follows, by Grignard addition at the ketone of 3. The Grignard reagent must be a salt of a divalent cation, e.g. $Mg^{++}$ or $Zn^{++}$. Monovalent cations are found unsuitable, such as $Li^+$ or $Na^+$. Suitable solvents include but are not limited to THF or ether. A wide range of temperature conditions are allowed between about 0° C. and about room temperature.

Ring closure to produce the compounds of the present invention 5 is accomplished with condensing agents such as 1,1'-carbonyldiimidazole, phosgene, dimethylcarbonate, diphenylcarbonate, or di-(paranitrophenyl)carbonate. Cyclization can be accomplished with any of these compounds, as well as a wide variety of others.

A specific instance of Scheme I is provided in Scheme IA. It charts the synthesis of L-741,211, which is a racemate of Compound 37.2, as further provided in Example 6.

SCHEME IA

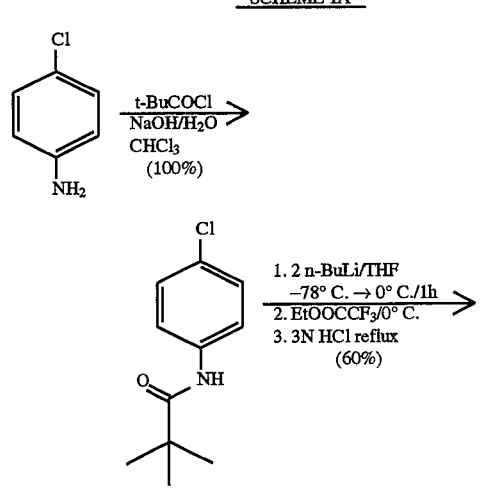

-continued
SCHEME IA

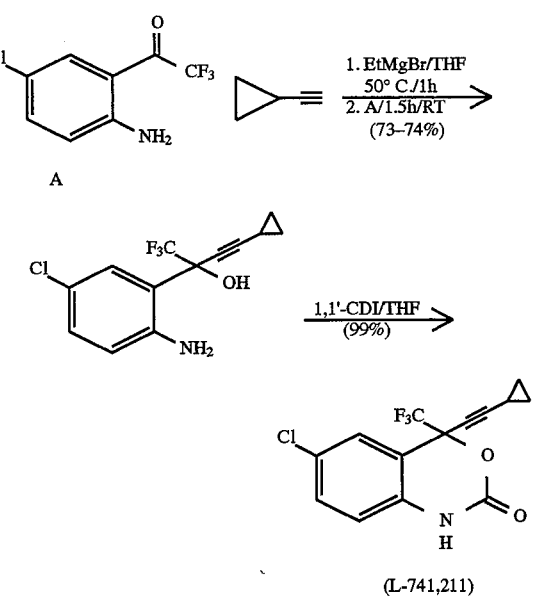

(L-741,211)

SCHEME II

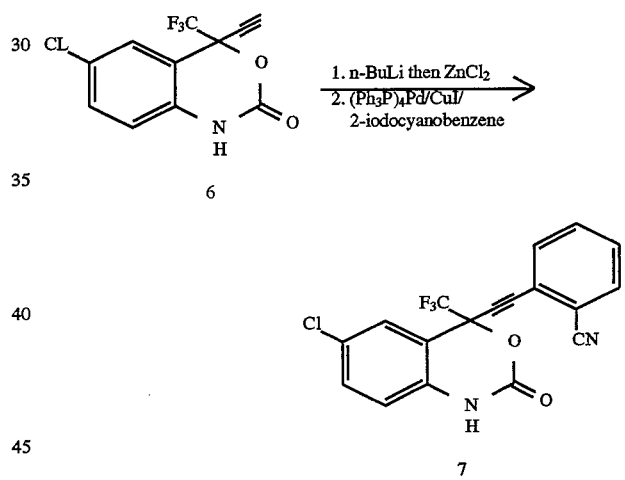

Scheme II provides one method for derivatizing acetylene substitutions at the 4-position of the benzoxazine nucleus. By way of illustration, Compound 6 is metalized, then a zinc salt is added. In the Heck reaction the catalyst tetrakis (triphenylphosphine)palladium(0) omplexed with CuI is employed to give 7.

SCHEME III

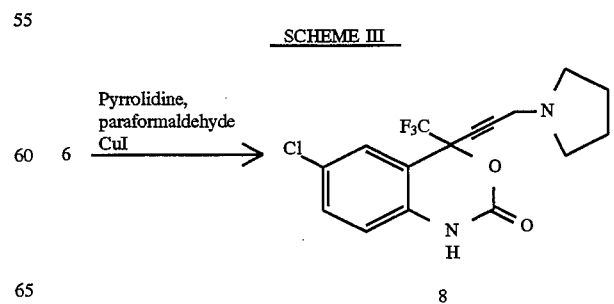

Scheme III illustrates substitution of a 4-acetylene group with an N-containing heterocycle. The Mannich reaction involves a condensation reaction of formaldehyde with the heterocycle, e.g. pyrrolidine. Substitution on the terminal carbon follows in the presence of CuI as catalyst.

SCHEME IV

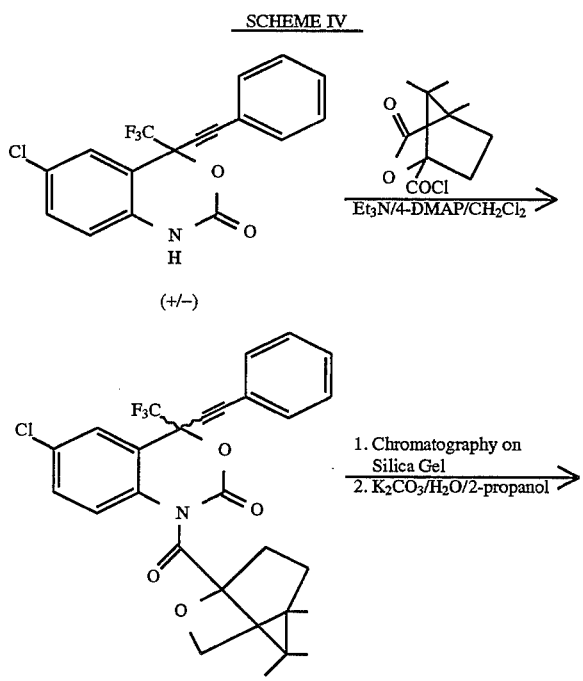

Scheme IV illustrates the resolution of optical isomers of the compounds of Formula I or Formula II. In this example, (−) camphanic acid is the resolving agent. A wide variety of other resolving agents are suitable, including O-methyl mandelic acid chloride or Mosher's reagent. It is apparent to the skilled artison how to separate such isomers.

Scheme IVA is specifically adapted to the resolution of L-741,211 in the isolation of L-743,726. See Scheme IVA, and Example 6.

SCHEME IVA

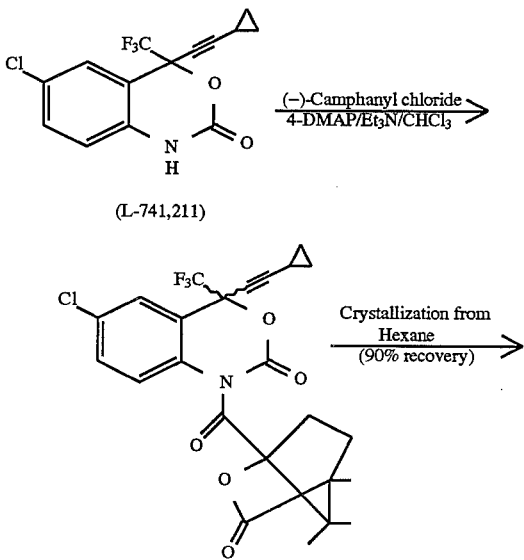

-continued
SCHEME IVA

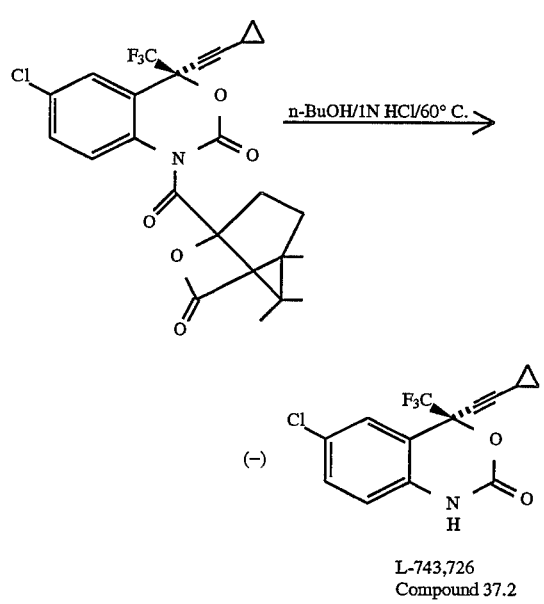

L-743,726
Compound 37.2

SCHEME V

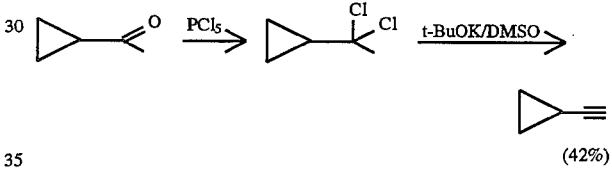

(42%)

Cyclopropyl acetylene is prepared by Scheme V in accordance with published procedures, e.g. C. E. Hudson et al., J. Am. Chem. Soc. 94, 1158 (1972) and W. Schoberth et al., Synthesis, 703 (1972).

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV reverse transcriptase, e.g., by competitive inhibition. Thus the compounds of this invention are commercial products to be sold for these purposes.

The compounds of the present inventions are useful in the inhibition of HIV reverse transcriptase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The particular advantage of the compounds of this invention is their potent inhibition against HIV reverse transcriptase rendered resistant to other antivirals, such as L-697,661, which is 3-([(4,7-dichloro-1,3-benzoxazol-2-yl)

methyl]-amino)-5-ethyl-6-methyl-pyridin-2(1H)-one; or L-696,229, which is 3-[2-(1,3-benzoxazol-2-yl)ethyl]-5-ethyl-6-methyl-pyridin-2(1H)-one; or AZT.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The compounds of this invention can be administered orally to humans in a dosage range of 1 to 100 mg/kg body weight in divided doses. One preferred dosage range is 0.1 to 10 mg/kg body weight orally in divided doses. Mother preferred dosage range is 0.1 to 20 mg/kg body weight orally in divided doses. For combination therapy with nucleoside analogs, a preferred dosage range is 0.1 to 20 mg/kg body weight for the compounds of this invention administered orally in divided doses, and 50 mg to 5 g/kg body weight for nucleoside analogs administered orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV reverse transcriptase inhibitor compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following Table.

TABLE

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxy-thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc. (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with |

TABLE-continued

| Drug Name | Manufacturer | Indication |
|---|---|---|
| Antibody which neutralizes pH labile alpha aberrant Interferon in an immuno-adsorption column | Advanced Biotherapy Concepts Rockville, MD) | AZT. AIDS, ARC |
| L-697,661 | Merck (Rahway, NJ) | AIDS, ARC, asymptomatic HIV positive, also in combination with AZT. |
| L-696,229 | Merck (Rahway, NJ) | AIDS, ARC, asymptomatic HIV positive, also in combination with AZT. |
| L-735,524 | Merck (Rahway, NJ) | AIDS, ARC, asymptomatic HIV positive, also in combination with AZT. |
| IMMUNO-MODULATORS | | |
| AS-101 | Wyeth-Ayerst Labs. (Philadelphia, PA) | AIDS |
| Bropirimine | Upjohn (Kalamazoo, MI) | advanced AIDS |
| Acemaman | Carrington Labs, Inc. (Irving, TX) | AIDS, ARC (See also antivirals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also antivirals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Somerville, NJ) Immunex (Seattle, WA) | AIDS |
| Granulocyte Macrophage Colony Stimulating Factor | Schering-Plough (Madison, NJ) | AIDS |
| HIV Core Particle Immunostimulant | Rorer (Ft. Washington, PA) | AIDS, in combination w/AZT seropositive HIV |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Scheming Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant | Genentech (S. San Francisco, CA) | AIDS, ARC |
| Rocombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazolec Pastille | Pfizer (New York, NY) | cryptococcal meningitis, candidiasis prevention of oral candidiasis |
| Nystatin Pastille | Squibb Corp (Princeton, NJ) | |
| Ornidyl Eflornithine | Merrell Dow (Cincinnati, OH) | PCP |
| Pentamidine Isethionate (IM & IV) | LyphoMed (Rosemont, IL) | PCP treatment |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ.) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS. For example, a compound of Formula I or Formula II may be suitably administered in combination with a nucleoside analog having known biological activity against HIV reverse transcriptase. Appropriate nucleoside analogs are generally chain terminators and include AZT, ddC, ddI, D4T, HEPT and 3'-fluoro-2',3'-dideoxythymidine.

AZT is synthesized by the methods of J. P. Horwitz et al., J. Org. Chem. 29, 2076 (1964); R. P. Glinski et al., J. Org. Chem. 38, 4299 (1973); C. K. Chu et al., Tetrahedron Letters 29, 5349 (1988). Application of AZT as a therapeutic drug in the treatment of AIDS is disclosed in U.S. Pat. No. 4,724,232.

The compound ddC is synthesized by the methods of J. P. Horwitz et al., J. Org. Chem. 32, 817 (1967); R. Marumoto, Chem. Pharm. Bull. 22, 128 (1974); and T.-S. Lin et al., J. Med. Chem. 30, 440 (1987).

D4T is synthesized by the methods of Herdewijn, P. et al., J. Med. Chem. 30, 1270 (1987).

HEPT is synthesized by the methods of Miyasaka, T. et. al. J. Med. Chem. 32, 2507 (1989); and A. Rosowsky, J. Med. Chem. 24, 1177 (1981). The synthesis of ddC, ddI and AZT are also described in EPO 484071.

The compound 3'-fluoro-2',3'-dideoxythymidine is synthesized by the procedures of Herdewijn, P. et al., J. Med. Chem. 30, 1270 (1987). The compound L-735,524 is N-(2 (R)-hydroxy-1(S)-indanyl)-2(R)-phenylmethyl-4-(S)-hydroxy-5-(1-(4-(3-pyridylmethyl)-2(S)-N'-(t-butylcarbamoyl)-piperazinyl))-pentaneamide, or pharmaceutically acceptable salt thereof. L-697,661 or '661' is 3-([4,7-dichloro-1,3-benzoxazol-2-yl)methyl]-amino)-5-ethyl-ethyl-6-methyl-pyridin-2(1H)-one; L-696,229 is 3-[2-(1,3-benzoxazol-2-yl)-ethyl]-5-ethyl-6-methyl-pyridin-2 (1H)-one. The synthesis of L-697,661 and L-696,229 is described in EPO 484071, and EPO 462800, both herein incorporated by reference. L-735,524 is synthesized by the methods of EP 0541168, herein incorporated by reference for these purposes.

Preferred combinations are simultaneous, intermittent, or alternating treatments of L-743,726 with or without an inhibitor of HIV protease. An optional third component in the combination is a nucleoside inhibitor of HIV reverse transcriptase, such as AZT, ddC or ddI. A preferred inhibitor of HIV protease is L-735,524. Other preferred inhibitors of HIV reverse transcriptase include L-697,661. These combinations may have synergistic effects on limiting the spread of HIV. Preferred combinations include the following: (1) L-743,726 with L-735,524, and, optionally any of L-697, 661, AZT, ddI or ddC; (2) L-743,726 and any of L-697,661, AZT, ddI or ddC. Pharmaceutically acceptable salts of these combinations are also included.

EXAMPLE 1

(+/−) 4-(1,1,1,-trifluoromethyl)-4-(1-buten-4-yl) -6-chloro-1,4-dihydro-2H-3,1-benzoxazin-2-one;
(Compound 15)

Step A: N-(4-chlorophenyl)-2,2-dimethylpropanamide

To a 5L 3 necked round bottomed flask with an overhead stirrer was added 4-chloroaniline (127.57 g, 1 mole), 1200 mL of CHCl₃, and 1200 mL of saturated aqueous Na₂CO₃ solution. An addition funnel was attached to the flask and charged with 2,2-dimethylpropanoyl chloride (129 mL, 1.05 mole). The acid chloride was added dropwise to the vigorously stirred mixture over 1 h. The resulting mixture was stirred at ambient temperature for an additional 23 h. Some of the product separated from the mixture as white crystals. These crystals were collected by filtration. The filtrate was transferred to a separatory funnel and the layers were separated. The chloroform layer was washed with water and brine. Drying (MgSO₄), filtration, and removal of the solvent in vacuo gave additional product. The two portions of product were combined and recrystallized from boiling EtOAc-hexanes to give 185.6 g of N-(4-chlorophenyl)-2,2-dimethyl propanamide as a white crystalline solid.

Step B 1-(2-amino-5-chlorophenyl)-2,2,2-trifluoroethanone

To an oven dried, 3 L, 3 necked round bottomed flask with an overhead stirrer, argon inlet, and a 500 mL oven dried addition funnel was added N-(4-chlorophenyl)-2,2-dimethylpropanamide (100 g, 472 mmol) and dry THF (1 L). This solution was cooled in an ice bath to 0° C. and the addition funnel was charged with n-butyllithium (387 mL of a 2.5M solution in hexanes, 968 mmol). The n-butyllithium solution was added dropwise to the amide solution slowly over 1 h, maintaining the temperature below +5° C. The resulting solution was aged at 0° C. for 1 h during which time an orange precipitate formed. To this mixture was added ethyl 1,1,1-trifluoroacetate (115 mL, 968 mmol), dropwise over 1 h. The resulting clear solution was aged an additional 30 min. The reaction was quenched with 5% aqueous HCl. The mixture was diluted with 1 L of EtOAc and the layers were separated. The organic phase was washed with brine, dried (MgSO₄), filtered and concentrated in vacuo, to give 160 g of a yellow oil. This material was suspended in 1 L of 3N aqueous HCl and the solution was heated at reflux for 24 h. The cooled solution was diluted with 1 L of EtOAc and the mixture was made basic with concentrated NH₄OH. The layers were separated and the organic phase was washed with brine, dried (MgSO₄), filtered, concentrated in vacuo, and chromatographed on 1.5 kg of silica gel using 15% EtOAc in hexane as eluant. The chromatographed material was recrystallized from boiling hexane to give 57 g (54%) of pure 1-(2-amino-5-chlorophenyl)-2,2,2-trifluoroethanone as bright yellow crystals, mp: 91°–92° C. $^1$H NMR (CDCl₃): δ6.46 (br s, 2H), 6.69 (d, 1H, J=9.2 Hz), 7.32 (dd, 1H, J=2.4, 9.2 Hz), 7.70 (d, 1H, J=2.4 Hz).

Step C (+/−) 2-(2-Amino-5-chlorophenyl)-1,1,1-trifluoro-5-hexen-2-ol

To a 300 mL oven dried 3 necked, round bottomed flask with a stirring bar, argon inlet, addition funnel and a reflux condenser was added magnesium (turnings, 3.03 g, 125 mmol) and dry THF (75 mL). To this well stirred mixture was added 4-bromo-1-butene (12.0 mL, 118.21 mmol) at such a rate as to maintain a gentle reflux. When the addition was complete, the mixture was aged 30 min then cooled to 0° C. in an ice bath. To this well stirred solution was added a solution of 1-(2-amino-5-chlorophenyl)-2,2,2-trifluoroethanone (5.00 g, 22.36 mmol) in THF (35 mL), dropwise over 30 min. The cooling bath was allowed to expire and the mixture was stirred 20 h at ambient temperature. The reaction was diluted with EtOAc and 10% aqueous citric acid. This mixture was stirred for 4 h. The layers were separated and the organic phase was washed with aqueous NaHCO₃ and brine. Drying (MgSO₄), filtration, removal of the solvent in vacuo, and chromatography on 300 g of silica gel using 15% EtOAc in hexane as eluantas eluant gave 4.80 g of (+/−) 2-(2-amino-5-chlorophenyl)-1,1,1-trifluoro-5-hexen-2-ol as a yellow solid.

Step D (+/−) 4-(1,1,1,-trifluoromethyl)-4-(1-buten-4-yl)-6-chloro-1,4-dihydro-2H-3,1-benzoxazin-2-one To a 200 mL round bottomed flask with a stirring bar, argon inlet and a reflux condenser was added. (+/−) 2-(2-Amino-5-chlorophenyl)-1,1,1-trifluoro-5-hexen-2-ol (4.80 g, 17.16 mmol), 1,1 '-carbonyldiimidazole (13.91 g, 85.81 mmol) and dry THF (75 mL). This mixture was heated at 60° C. for 18 h. The cooled reaction mixture was diluted with EtOAc and washed with H₂O (3×200 mL) and brine (250 mL). Drying (MgSO₄), filtration, removal of the solvent in vacuo, followed by recrystallization from boiling EtOAc-hexane gave 3.22g of (+/−) 4-(1,1,1-trifluoromethyl)-4(1-buten-4-yl)-6-chloro-1,4-dihydro-2H-3,1-benzoxazin-2-one as a white crystalline solid, mp: 165°–166° C. $^1$H NMR (CDCl$_3$): δ1.99 (m, 1H), 2.09–2.40 (m, 3H), 5.00 (d, 1H, J=1.4 Hz), 5.03 (dd, 1H, J=1.4, 7.9), 5.78 (m, 1H), 6.85 (d, 1H, J=8.6 Hz), 7.21 (br s, 1H), 7.35 (dd, 1H, J=2.2, 8.6 Hz), 9.63 (br s, 1H).

EXAMPLE 2

(+/−) 6-Chloro-4-ethynyl-4-(1,1,1-trifluoromethyl)-1,4-dihydro-2H-3,1-benzoxazin-2-one (Compound 26)

Step A 2-(2-amino-5-chlorophenyl)-1,1,1-trifluoro-3-butyn-2-ol

A 500 ml 3-neck round bottom flask fitted with an addition funnel, argon inlet, stirring bar and digital thermometer was charged with ethynyl magnesium bromide (0.5M in hexane; 268 mL, 134 mmol) then chilled to −78° C. Dropwise addition of a solution of 1-(2-amino-5-chlorophenyl)-2,2,2-trifluororethanone (6.0 g, 26.8 mmol) in 50 mL THF was completed after 15 minutes keeping the temperature <−55° C. The reaction mixture was stirred for 16 h after slowly warming to room temperature. The dark red solution was quenched at −5° C. by dropwise addition of saturated aqueous ammonium chloride solution (60 mL). Ethyl acetate extraction followed by washes of 10% citric acid, saturated sodium bicarbonate, water and brine afforded 8.5 g crude product after drying over sodium sulfate, filtration, and evaporation of solvent. Purification via flash chromatography using 15–20% ethyl acetate: hexane afforded pure 2-(2-amino-5-chlorophenyl)-1,1,1-trifluoro-3-butyn-2-ol (5 g light brown oil, 75% yield).

Step B (+/−) 6-Chloro-4-ethynyl-4-(1,1,1-trifluoromethyl)-1,4-dihydro-2H-3,1-benzoxazin-2-one A THF solution of 2-(2-amino-5-chlorophenyl)-1,1,1-trifluoro-3-butyn-2-ol (5.0 g, 20.0 mmol in 225 mL THF) was treated with 1,1'-carbonyldiimidazole (13.0 g, 80.0 mmol) and heated in an oil bath at 60° C. for 17 h. The THF was removed in vacuo, the residue dissolved in ethyl acetate then washed with 10% citric acid, sodium bicarbonate, water and brine before drying over sodium sulfate. Following filtration and evaporation in vacuo the crude product was isolated (3.6 g) and recrystallized from ethyl acetate: hexane. The product (+/−) 6-chloro-4-ethynyl-4-(1,1,1-trifluoromethyl)-1,4-dihydro-2H-3,1-benzoxazin-2-one was isolated as a white crystalline solid (3.22 g, 58.4% yield): mp 226°–227° C. $^1$H-NMR (CDCl$_3$+trace DMSO): δ3.16 (s, 1H), 6.98 (d, J=3.3 Hz, 1H), 7.35 (m, 1H), 7.51 (s, 1H), 10.66 (s, 1H).

EXAMPLE 3

(+/−) 6-Chloro-4-(1,1,1-trifluoromethyl)-4-[(3-(1-pyrrolidinyl))-1-propynyl]-1,4-dihydro-2H-3,1-benzoxazin-2-one (Compound 7)

A dioxane solution of (+/−)6-chloro-4-ethynyl-4-(1,1,1-trifluoromethyl)-1,4-dihydro-2H-3,1-benzoxazin-2-one (150 mg, 0.544 mmol), pyrrolidine (52.2 μL, 0.626 mmol), paraformaldehyde (20.5 mg, 0.681 mmol), acetic acid (31.1 μL, 0.544 mmol) and copper (I) chloride (20.5 mg, 0.207 mmol in 3.5 ml dioxane) was heated to 50° C. in an oil bath for approximately 2 h. The reaction mixture was quenched into 2N HCl and extracted with ethyl acetate. The aqueous layer was neutralized with solid potassium carbonate and extracted with ethyl acetate (3x). The combined extracts were washed with water and brine before drying over sodium sulfate to afford 140 mg crude product. Chromatographic purification on silica gel and recrystallization from ethyl acetate: hexane afforded crystalline (+/−) 6-chloro-4-(1,1,1-trifluoromethyl)-4-[(3-(1-pyrrolidinyl))-1-propynyl]-1,4-dihydro-2H-3,1-benzoxazin-2-one (89 mg, 46% yield): MP 160°–161° C. (dec). $^1$H-NMR (CDCl$_3$): δ1.85–1.89 (m, 4H), 2.68–2.71 (m, 4H), 3.67 (s, 1H), 6.88 (d, J=8.55 Hz, 1H), 7.40 (dd, J=2.19, 8.54 Hz, 1H), 7.55 (s, 1H), 9.45 (s, 1H).

(+/−) 6-Chloro-4-(2-cyanophenyl)ethynyl-4-(1,1,1-trifluoromethyl)-1,4-dihydro-2H-3,1-benzoxazin-2-one (Compound 2)

A solution of 6-Chloro-4-ethynyl-4-(1,1,1-trifluoromethyl)-1,4-dihydro-2H-3,1-benzoxazin-2-one (138 mg, 0.5 mmol) in 3 mL of dry THF was stirred at −78° C. To this solution was added 0.4 mL (1.0 mmol) of n-butyllithium, 2.5M in hexane. The anion was aged for 10 minutes at −78° C. then 1 mL of ZnCl$_2$(1M in ether) solution was added. The reaction mixture was allowed to stir at −78° C. for 15 minutes, the ice bath was removed and the mixture slowly warmed to 0° C. over 30 min. To the reaction mixture was added a solution of 2-iodobenzonitrile (149 mg, 0.65 mmol) in 2 mL THF, followed by tetrakis(triphenylphosphine) palladium(0) (56 mg, 0.05 mmol). The reaction was allowed to warm to r.t. and continued to stir over 15 hours. The reaction mixture was quenched with 10 mL of 2N HCl, extracted with 2×200 mL EtOAc and the combined extracts were washed with H$_2$O, brine and dried over MgSO$_4$. The solvent was removed to give 195 mg of an oil which was flashed chromatographed on silica gel (20% EtOAc in hexane) to afford 60 mg of the unreacted starting material and 35 mg of the coupled product. The latter was triturated with ether to yield 25 mg of (+/−) 6-Chloro-4-(2-cyanophenyl)ethynyl-4-(1,1,1-trifluoromethyl)-1,4-dihydro-2H-3,1-benzoxazin-2-one. mp: 245°–246° C. FAB. MS M+1=377 m/e. $^1$H NMR (CDCl$_3$): δ6.82–6.85 (d, J=8.5 Hz, 1H); 7.40–7.44 (dd, J=2.1, 8.5 Hz, 1H); 7.56–7.79 (m, 5H); 8.00 (s, 1H).

EXAMPLE 4

(+/−) 4-(1-Chloro-1,1-difluoromethyl)-4-(2-phenylethynyl)-6-chloro-1,4-dihydro-2H-3,1-benzoxazin-2-one (Compound 5)

Step A 1-(2-amino-5-chlorophenyl)-2-chloro-2,2-difluoroethanone

To an oven dried, 300 mL, 3 necked round bottomed flask with a magnetic stirring bar, argon inlet, and a 100 mL oven dried addition funnel was added N-(4-chlorophenyl)-2,2-dimethyl-propanamide (10 g, 47.2 mmol) and dry THF (100 mL). This solution was cooled in an ice bath to 0° C. and the addition funnel was charged with n-butyllithium (38.7 mL of a 2.5M solution in hexanes, 96.8 mmol). The n-butyllithium solution was added dropwise to the amide solution slowly over 1 h, maintaining the temperature below +5° C. The resulting solution was aged at 0° C. for 1 h during which time an orange precipitate formed. To this mixture was added ethyl 1-chloro-1,1-difluoroacetate (10.2 mL, 96.8 mmol), dropwise over 15 min. The resulting clear solution was aged an additional 30 min. The reaction was quenched with 5% aqueous HCl. The mixture was diluted with 1 L of EtOAc and the layers were separated. The organic phase was washed with brine, dried (MgSO₄), filtered and concentrated in vacuo, to give 160 g of a yellow oil. This material was suspended in 200 mL of 3N aqueous HCl and the solution was heated at reflux for 24 h. The cooled solution was diluted with 500 mL of EtOAc and the mixture was made basic with concentrated NH₄OH. The layers were separated and the organic phase was washed with brine, dried (MgSO₄), filtered, concentrated in vacuo, and chromatographed on 350 g of silica gel using 15% EtOAc in hexane as eluant. The chromatographed material was recrystallized from boiling hexane to give 5.5 g of pure 1-(2-amino-5-chlorophenyl)-2-chloro-2,2-difluoroethanone as bright yellow crystals, mp: 55°–56° C. $^1$H NMR (CDCl₃): δ6.43 (br s, 2H), 6.69 (d, 1H, J=9.0 Hz), 7.31 (dd, 1H, J=2.4, 9.0 Hz), 7.80 (d, 1H, J=2.4 Hz).

Step B (+/−) 2-(2-amino-5-chlorophenyl)-4-phenyl-1-chloro-1,1-difluoro-3-butyn-2-ol To a 100 mL, 3 necked, oven dried round bottomed flask, with a stirring bar, argon inlet, reflux condenser, and a septum was added ethynyl benzene (2.13 g, 20.83 mmol), dry THF (50 mL) and ethyl magnesium bromide (6.94 mL of a 3.0M solution in ether). This mixture was aged 2 h at ambient temperature then a solution of 1-(2-amino-5-chlorophenyl)-2-chloro-2,2-difluoroethanone (1.00 g, 4.17 mmol) in THF (6 mL) was added with a syringe. The resulting orange-red solution was stirred at ambient temperature for 21.5 h. The reaction was quenched by addition of 1N HCl (50 mL) then diluted with EtOAc. The solution was then made basic with concentrated NH₄OH and the layers were separated. The organic phase was washed with water and brine. Drying (MgSO₄), filtration, removal of the solvent in vacuo, and chromatography on silica gel using 20% EtOAc in hexane as eluant gave 1.02 g of (+/−) 2-(2-amino-5-chlorophenyl)-4-phenyl-1-chloro-1,1-difluoro-3-butyn-2-ol as an off white solid. $^1$H NMR (CDCl₃): δ4.42 (br s, 2H), 5.10 (br s, 1H), 6.65 (d, 1H, J=8.5 Hz), 7.15 (dd, 1H, J=2.4, 8.5 Hz), 7.38 (m, 3H), 7.55 (m, 2H), 7.70 (d, J=2.4 Hz).

Step C (+/−) 4-(1-Chloro-1,1-difluoromethyl)-4-(2-phenyl-ethynyl)-6-chloro-1,4-dihydro-2H-3, 1-benzoxazin-2-one To a 100 mL round bottomed flask with a stirring bar, reflux condenser, and an argon inlet was added (+/−) 2-(2-amino-5-chlorophenyl)-4-phenyl-1-chloro-1,1-difluoro-3-butyn-2-ol (0.81 g, 2.37 mmol), dry THF (25 mL), and 1,1'-carbonyldiimidazole (1.919 g, 11.84 mmol). This solution was heated at 60° C. for 20 h. The cooled reaction mixture was diluted with EtOAc and washed with 0.5N HCl, H₂O, and brine. Drying (MgSO₄), filtration, and removal of the solvent in vacuo gave 890 mg of an oil. This material was chromatographed on 80 g of silica gel using 20% EtOAc in hexane as eluant. The chromatographed material was recrystallized from boiling EtOAc-hexanes to give 507 mg. (58%) of (+/−) 4-(1-chloro-1,1-difluoromethyl)-4-(2-phenylethynyl)-6-chloro-1,4-dihydro-2H-3,1-benzoxazin-2-one as white needles, mp: 154°–155° C. $^1$H NMR (CDCl₃): δ6.89 (d, 1H, J=8.4 Hz), 7.35–7.48 (m, 4H), 7.56 (m, 2H), 7.64 (br s, 1H), 9.19 (br s, 1H).

EXAMPLE 5

(−)6-Chloro-4-phenylethynyl-4-trifluoromethyl,1,4-dihydro-2H-3,1-benzoxazin-2-one (Compound 4)

Step A 2-(2-Amino-5-chlorophenyl)-4-phenyl-1,1,1-trifluoro-3-butyn-2-ol

A solution of lithio phenylacetylide, prepared from 4.83 mL of phenylacetylene (0.044 mol) and 17.2 mL of a 2.5N solution of n-butyllithium in hexane (0.043 mol) in 50 mL of THF at −78° C., was treated with 11.4 g of magnesium bromide etherate (0.044 mol) over 5 minutes. The mixture was allowed to warm to −20° C. and stirring under argon was continued for 30 minutes. The mixture was then cooled to −60° C. and a solution containing 2.5 g (0.011 mol) of 1-(2-amino-5-chloro)-2,2,2-trifluoromethylethanone, previously complexed with an equivalent (2.8 g, 0.011 mol) of magnesium bromide etherate in 25 mL of THF, was added. The reaction mixture was allowed to stir at 15° for one hour before being cooled to 0° C. and treated dropwise with a mixture of 30 mL each of saturated aqueous ammonium chloride solution and water. The mixture was extracted with 2×100 mL portions of ethyl ether, the combined organic phases were washed with brine and dried over MgSO₄. Removal of the drying agent and solvents left 6 g of an oil which was flash chromatographed on silica gel, eluting with 20% EtOAc in hexane, to afford 2.5 g of 2-(2-amino-5-chloro-phenyl)-4-phenyl-1,1,1-trifluoro-3-butyn-2-ol. $^1$H-NMR (CDCl₃): δ4.63 (br s, 3H), 6.69 (d, J=8.5 Hz, 1H), 7.15 (d, J=2 Hz, 1H), 7.17 (d, J=2 Hz, 1H), 7.35–7.44 (m, 3H), 7.53–7.56 (m, 2H), 7.66 (d, J=2 Hz, 1H). FAB MS M+H=326 m/e.

Step B (+) 6-Chloro-4-phenylethynyl-4-trifluoromethyl-1,4-dihydro-2H-3,1-benzoxazin-2-one (Compound 12)

A solution of 2-(2-amino-5-chlorophenyl)-4-phenyl-1,1,1-trifluoro-3-butyn-2-ol (2.0 g, 6.1 mmol) and 11.0 g (12.0 mmol) of 1,1'-carbonyldiimidazole in 300 mL of dry THF was stirred under argon at 55° C. for 24 hours. The solvent was removed on a rotary evaporator and the residue was partitioned between 200 mL of ether and 400 mL of water. The layers were separated and the aqueous extracted once more with ether. The combined ether extracts were washed with 2×200 mL 10% citric acid and then with brine before drying over MgSO₄. Removal of the drying agent and solvent provided 1.5 g (70%) of the crude title compound as an oil. Trimration with ether-hexane afforded 875 mg of (±) 6-chloro-4-phenylethynyl-4-trifluoromethyl-1,4-dihydro-2H-3,1-benzoxazin-2-one as a white solid, partial melt at 137°, clear at 147° C. $^1$H-NMR (CDCl₃): δ6.92 (d, J=8 Hz, 1H), 7.30–7.49 (m, 4H), 7.58–7.65 (m, 3H), 8.99 (s, 1H).

Step C

6-Chloro-1-(1S)-camphanoyl-4-phenylethynyl-4-trifluoro-methyl-1,4-dihydro-2H-3,1-benzoxazin-2-one To a solution containing (±) 6-chloro-4-phenylethynyl-4-trifluoromethyl-1,4-dihydro-2H-3,1-benzoxazin-2-one (2.24 g, 6.37 mmol), 4-dimethylaminopyridine (0.10 g, 0.8 mmol), and (−) camphanic acid chloride (2.07 g, 9.55 mmol) in 60 mL of dry dichloromethane, stirred under argon in an ice bath, was added triethylamine (2.22 mL, 15.9 mmol). The cooling bath was removed and the reaction was allowed to proceed at room temperature. When the reaction was complete by thin layer chromatography ($SiO_2$, 4% EtOAc in $CHCl_3$), the solution was diluted with 200 mL of $CHCl_3$ and washed twice with 10% citric acid, then with brine. Upon drying ($MgSO_4$) the solvent was removed on a rotary evaporator and the foamy reside was subjected to flash chromatography, eluting with $CHCl_3$. There was obtained 575 mg of diastereomer I of 6-chloro-(1S)-camphanoyl-4-phenylethynyl-4-trifluoromethyl-1,4-dihydro-2H-3,1-benzoxazin-2-one as an oil, $^1$H-NMR ($CDCl_3$): δ0.85 (s, 3H), 1.08 (s, 3H), 1.22 (s, 3H), 1.73–1.85 (m, 1H), 1.92–2.08 (m, 1H), 2.50–2.67 (m, 2H), 7.30–7.79 (m, 8H). This was followed by 1.52 g of mixed fractions (diastereomers I and II). Continued elution afforded 680 mg of the slower-moving diastereomer (II) of the title compound which, upon trituration with an ether/hexane mixture, gave clumps of white needles, mp 177°–178.5° C.; $^1$H-NMR ($CDCl_3$): δ0.83 (s, 3H), 1.12 (s, 3H), 1.23 (s, 3H), 1.73–1.86 (m, 1H), 1.93–2.06 (m, 1H), 2.50–2.63 (m, 2H), 7.38–7.51 (m, 4H), 7.49–7.62 (m, 2H), 7.72 (d, J=9 Hz, 1H), 7.76 (d, J=2 Hz, 1H).

The 1.52 g of isomer mixture from the flash chromatography was dissolved in 75 mL of ether, the solution diluted with 50 mL of hexane, and then seeded with a crystal of isomer II. Slow crystallization afforded an additional 385 mg of isomer II which was recrystallized from ether/hexane to give >96% diastereomerically pure material by HPLC.

Step D (−) 6-Chloro-4-phenylethynyl-4-trifluoromethyl-1,4-dihydro-2H-3,1-benzoxazin-2-one The crystalline diastereomer(II) of 6-chloro-1-(1S)-camphanoyl-4-phenylethynyl-4-trifluoromethyl-1,2-dihydro-4(H)-3,1-benzoxazin-2-one (53 mg, 0.10 mmol) was dissolved in 8 mL of 2-propanol at 45° C. under an atmosphere of argon. To the solution was added 0.27 mL of a 10% aqueous solution of $K_2CO_3$. Stirring was continued for 10 min., by which time all of the starting material had been consumed (TLC, $SiO_2$, 4% EtOAc in $CHCl_3$). The solution was concentrated in vacuo and the residue taken up in ether. After washing with 0.1N HCl and brine, the ether solution was dried ($MgSO_4$), filtered and evaporated in vacuo to an oily solid which was purified by $SiO_2$ chromatography, eluant 5% 2-propanol in hexane. (−) 6-Chloro-4-phenylethynyl-4-trifluoromethyl-1,4-dihydro-2H-3,1-benzoxazin-2-one was obtained as white needles from ether/hexane, m.p. 178°–179° C.; $[\alpha]_D 20 = -92.5°$ ($CHCl_3$, c=0.0012 g mL-1); $^1$H-NMR ($CDCl_3$): δ6.87 (d, J=8.5 Hz, 1H), 7.37–7.50 (m, 4H), 7.56–7.63 (m, 3H), 8.60 (s, 1H).

Step E (+) 6-Chloro-4-phenylethynyl-4-trifluoromethyl 1,4-dihydro-2H-3,1-benzoxazin-2-one (Compound 3)

(+) 6-Chloro-4-phenylethynyl-4-trifluoromethyl-1,4-dihydro-2H-3,1-benzoxazin-2-one was prepared from the non-crystalline product of Step C, diastereomer I, in a manner according to Step D: m.p. 178°–179° C.; $[\alpha]_D^{20}=+87.6°$ ($CHCl_3$, c=0.0050 g mL-1; $^1$H-NMR($CDCl_3$): δ6.87 (d, J=8.5 Hz, 1H), 7.37–7.50 (m, 4H), 7.56–7.63 (m, 3H), 8.60 (s, 1H).

EXAMPLE 6

(−) 6-Chloro-4-cyclopropylethynyl-4-trifluoromethyl-1,4-dihydro-2H-3,1-benzoxazin-2-one(L-743,726, Compound 37.2) and (+)6-Chloro-4-cyclopropylethynyl-4-trifluoromethyl-1,4-dihydro-2H-3,1-benzoxazin-2-one (L-743,725)

Step A 2-(2-Amino-5-chlorophenyl)-4-cyclopropyl-1,1,1-trifluoro-3-butyn-2-ol

A solution of bromomagnesium cyclopropylacetylide, was prepared from 23 g of cyclopropylacetylene (0.348 mol) in 250 mL of THF by dropwise addition of 116 mL of a 3.0M solution of ethylmagnesium bromide in ether (0.348 mol) over 1 h. This solution was maintained at 0° C. for 1 h, then at 40° C. for 3 h. To this solution, recooled to 0° C., 15.56 g of 1-(2-amino-5-chlorophenyl)-2,2,2-trifluoromethylethanone (0.0696 mol), was added as a solid, portionwise over 5 min. The reaction mixture was allowed to stir at 0° for 1.5 hours. The reaction was quenched at 0° C. by dropwise addition of 700 mL of saturated aqueous ammonium chloride solution. The mixture was extracted with 2×400 mL portions of ethyl acetate, the combined organic phases were washed with brine and dried over $MgSO_4$. Removal of the drying agent and solvents left a yellow solid. This material was recrystallized from boiling hexanes (100 mL final volume) to afford 14.67 g of 2-(2-amino-5-chlorophenyl)-4-cyclopropyl-1,1,1-trifluoro-3-butyn-2-ol. A second crop (2.1 g) was obtained from concentrating the mother liquors. mp: 153°–154° C. $^1$H-NMR ($CDCl_3$): δ0.84 (m, 2H), 0.90 (m, 2H), 1.38 (m, 1H), 4.50 (br s, 3H), 6.69 (d, J=8.5 Hz, 1H), 7.13 (dd, J=2.5, 8.5 Hz, 1H), 7.55 (d, J=2.5 Hz, 1H).

Step B (+) 6-Chloro-4-cyclopropylethynyl-4-trifluoromethyl-1,4-dihydro-2H-3,1-benzoxazin-2-one (L-741,211)

A solution of 2-(2-amino-5-chlorophenyl)-4-cyclopropyl-1,1,1-trifluoro-3-butyn-2-ol (15.00 g, 0.0518 mol) and 41.98 g (0.259 mol) of 1,1'-carbonyldiimidazole in 250 mL of dry THF was stirred under argon at 55° C. for 24 hours. The solvent was removed on a rotary evaporator and the residue was partitioned between 500 mL of ethyl acetate and 400 mL of water. The layers were. separated and the aqueous phase was extracted once more with ethyl acetate. The combined ethyl acetate extracts were washed with 2×200 mL of 2% aqueous HCl, saturated aqueous $NaHCO_3$, and brine. Drying over $MgSO_4$, filtration, and removal of the solvent in vacuo provided 16.42 g of the title compound as a solid. Recrystallization from ethyl acetate-hexane afforded 12.97 g of analytically pure (±) 6-chloro-4-cyclo-propylethynyl-4-trifluoromethyl-1,4-dihydro-2H-3,1-benzoxazin-2-one as a white crystals. mp: 178°–180° C. $^1$H-NMR ($CDCl_3$): 0.85 (m, 2H), 0.94 (m, 2H), 1.40 (m, 1H), 6.81 (d, J=8.5 Hz, 1H), 7.37 (dd, J=2.5, 8.5 Hz, 1H), 7.49 (d, J=2.5 Hz, 1H), 8.87 (br s, 1H).

Step C

6-Chloro-1-(1S)-camphanoyl-4-cyclopropylethynyl-4-trifluoromethyl-1,4-dihydro-2H-3,1-benzoxazin-2-one To a solution containing (±) 6-chloro-4-cyclopropylethynyl-4-trifluoromethyl-1,4-dihydro-2H-3,1-benzoxazin- 2-one (12.97 g, 0.041 mol), 4-dimethylaminopyridine (1.02 g, 0.0083 mol), and (−) camphanic acid chloride (14.22 g, 0.06556 mol) in 350 mL of dry dichloromethane, stirred under argon in an ice bath, was added triethylamine (22.84 mL, 0.164 mol). The cooling bath was removed and the reaction was allowed to proceed at room temperature. After 75 min. the reaction was judged complete by thin layer chromatography ($SiO_2$, 4% EtOAc in $CHCl_3$), and the solution was diluted with 500 mL of $CHCl_3$ then washed with 10% citric acid (2X), water (1X), and brine (1X). Drying ($MgSO_4$), filtration, and removal of the solvent in vacuo left a colorless foam. This material was triturated with 200 mL of boiling hexane. On cooling to room temperature the desired diastereomeric camphanate imide precipitated. The solid was collected on a frit, washed with a little cold hexanes and dried in vacuo to give 7.79g of 6-chloro-1-(1S)-camphanoyl-4-cyclopropylethynyl-4-trifluoromethyl-1,4-dihydro-2H-3,1-benzoxazin-2-one as white crystals. mp: 164°–165° C. HPLC purity: 99.2% @254 nm. $^1$H-NMR ($CDCl_3$): δ0.77 (s, 3H), 0.86–0.96 (m, 4H), 1.08 (s, 3H), 1.19 (s, 3H), 1.44 (m, 1H), 1.76 (m, 1H), 1.95 (m, 1H), 2.51 (m, 2H), 7.42 (dd, J=2.4,9.0 Hz, 1H), 7.63 (m, 2H).

Step D (−) 6-Chloro-4-cyclopropylethynyl-4-trifluoromethyl- 1,4-dihydro-2H-3,1-benzoxazin-2-one (L-743,726, Compound 37.2)

6-chloro-1-(1S) -camphanoyl-4-cyclopropylethynyl-4-trifluoromethyl-1,2-dihydro-4(H)-3,1-benzoxazin-2-one (7.50 g, 0.01512 mol) was dissolved in 150 mL of n-butanol at 60° C. under an atmosphere of argon. To this solution was added 10 mL of 1N HCl. This solution was maintained at 60° C. for 72 h. The mixture was neutralized with aqueous $NaHCO_3$ and the n-butanol was removed in vacuo. The residue was dissolved in 150 mL of THF and treated with 50 mL of 2N LiOH for 3 h at room temperature. This mixture was diluted with ethyl acetate and washed with two portions of water and one of brine. Drying ($MgSO_4$), filtration and removal of the solvent in vacuo gave a white solid. This material was recrystallized from hot hexane to give 3.43 g of (−) 6-chloro-4-cyclopropylethynyl-4-trifluoromethyl-1,4-dihydro-2H-3,1-benzoxazin-2-one as white crystals., m.p. 131°–132° C.; $[\alpha]_D^{20} = -84.7°$ ($CHCl_3$, c=0.005 g mL$^{-1}$); $^1$H-NMR ($CDCl_3$): a δ0.85 (m, 2H), 0.94 (m, 2H), 1.40 (m, 1H), 6.81 (d, J=8.5 Hz, 1H), 7.37 (dd, J=2.5, 8.5 Hz, 1H), 7.49 (d,J=2.5 Hz, 1H), 8.87 (br s, 1H).

Step E (+) 6-Chloro-4-cyclopropylethynyl-4-trifluoromethyl-1,4-dihydro-2H-3,1-benzoxazin-2-one (L-743,725)

The mother liquors from Step C above were purified by column chromatography on silica gel using 10% ethyl acetate in hexanes as eluant. The pure, undesired diastereomer (a colorless foam) was hydroylzed according to Step D. The enantiomeric benzoxazinone, (+) 6-Chloro-4-cyclopropylethynyl-4-trifluoromethyl-1,4-dihydro-2H-3,1-benzoxazin-2-one, was obtained as white crystals. m.p. 131°–132° C.; $[\alpha]_D^{20} = +84.4°$ ($CHCl_3$, c=0.005 g mL$^{-1}$); $^1$H-NMR ($CDCl_3$): δ0.85 (m, 2H), 0.94 (m, 2H), 1.40 (m, 1H), 6.81 (d, J=8.5 Hz, 1H), 7.37 (dd, J=2.5, 8.5 Hz, 1H), 7.49 (d, J=2.5 Hz, 1H), 8.87 (br s, 1H).

REVERSE TRANSCRIPTASE ASSAY

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C)·oligo d(G)$_{12-18}$. The inhibitors of the present invention inhibit this incorporation.

The assays were carried out in 55 mM Tris (pH 8.2)-30 mM KCl-30 mM $MgCl_2$-1 mM dithiothreitol-20 μg of rC:dG$_{12-18}$ (Pharmacia) per ml-8 mM [$^3$H]dGTP (New England Nuclear)-0.01% Triton X-100-50 mM ethylene glycol-bis(β-amino-ethyl ether)-N,N,N',N'-tetraacetic acid (EGTA)-1 mg of bovine serum albumin per ml. After 60 min of incubation at 37° C., acid-precipitable material was collected onto glass fiber filters by using a semiautomatic cell harvester. Bacterial cell extracts containing RT were diluted to within the linear range of the assay, and activity was determined in the presence and absence of inhibitor. Purified HIV-1 RT heterodimer produced in E. coli also served as a control. Results are determined as inhibitor concentration to give 50% inhibition ($IC_{50}$ wt), in nanomoles/liter.

For the double mutant assay (dm), A17 RT was employed in the assay. A17 RT is resistant to various aminopyridones, as described in Nunberg, J. H. et al., J. Virol. 65, 4887 (1991). Results are measured as $IC_{50}$ dm in nanomoles/liter.

CELL SPREAD ASSAY

Inhibition of the spread of HIV in cell culture was measured according to Nunberg, J. H. et al., J. Virol. 65, 4887 (1991). In this assay, MT-4 T-lymphoid cells were infected with HIV-1 (wild-type, unless otherwise indicated) by using a predetermined inoculum, and cultures were incubated for 24 h. At this time, <1% of the cells were positive by indirect immunofluorescence. Cells were then extensively washed and distributed into 96-well culture dishes. Serial twofold dilutions of inhibitor were added to the wells, and cultures were continued for 3 additional days. At 4 days postinfection, 100% of the cells in control cultures were infected. HIV-1 p24 accumulation was directly correlated with virus spread. The cell culture inhibitory concentration was defined as the inhibitor concentration in nanomoles/liter which reduced the spread of infection by at least 95%, or $CIC_{95}$.

| SUMMARY OF RESULTS FOR COMPOUND 37.2 | | | | | |
|---|---|---|---|---|---|
| A. Reverse Transcriptase Assay and Cell Spread Assay: | | | | | |
|  | WT | K103N* | Y181C | DM | RT-2 |
| $IC_{50}$(μM) | 0.002 | 0.030 | 0.008 | 0.085 | 80.8 |
| $CIC_{95}$(μM) | <0.006(N = 2) | 0.100 | <0.025 | 0.400 | N.D. |
| B. Pharmacological Data: | | | | | |

Rhesus: 1 mg kg$^{-1}$ i.v.: $t_{1/2}$ = 210 min.  
10 mg kg$^{-1}$ p.o.(methocel: $C_{max}$ = 4.4 μM @ 2 h  
$C_{24h}$ = 1.1 μM  
Protein Binding: 98.0% Normal Human Plasma (HPLC Method)

} O.B. = 0.55 (A.U.C.)

*Mutants K103N and Y181C are drug-resistant HIV-1 reverse transcriptases. DM is the double mutant, as discussed in the reverse transcriptase assay. RT-2 is the reverse transcriptase of HIV-2.

SYNERGISTIC EFFECTS

A. Preparation of HIV-Infected MT-4 Cell Suspension

MT cells were infected at Day 0 at a concentration of 250,000 per ml with a 1:1000 dilution of HIV-1 strain IIIb stock (final 125 pg p24/ml; sufficient to yield <1% infected cells on day 1 and 25–100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C in 5% $CO_2$ atmosphere.

B. Treatment with Inhibitors

A matrix of nanomolar range concentrations of the pairwise combinations (see Table S) was prepared. At Day 1, aliquots of 125 μl of inhibitors were added to equal volumes of HIV-infected MT-4 cells (50,000 per well) in a 96-well microtiter cell culture plate. Incubation was continued for 3 days at 37° C. in 5% $CO_2$ atmosphere.

C. Measurement of Virus Spread

Using a multichannel pipettor, the settled cells were resuspended and 125 μl harvested into a separate microtiter plate. The supernatant was assayed for HIV p24 antigen.

The concentration of HIV p24 antigen was measured by an enzyme immunoassay, described as follows. Aliquots of p24 antigen to be measured were added to microwells coated with a monoclonal antibody specific for HIV core antigen. The microwells were washed at this point, and at other appropriate steps that follow. Biotinylated HIV-specific antibody was then added, followed by conjugated strepavidin-horseradish peroxidase. A color reaction occurs from the added hydrogen peroxide and tetramethylbenzidine substrate. Color intensity is proportional to the concentration of HIV p24 antigen.

Calculation of Degree of Synergy

Pairwise combinations of inhibitors (see Table 5) were found to exhibit markedly enhanced inhibition of virus spread, in comparison to each inhibitor alone, or in comparison to merely additive inhibition of each inhibitor. Thus, for example, the pairwise combination of 726 and AZT was found to exhibit markedly enhanced inhibition of virus spread, in comparison to 726 alone or AZT alone, or in comparison to the sum of 726 inhibition and AZT inhibition.

This data was processed as follows: fractional inhibitory concentration ratios (FIC) were calculated according to Elion, et. al. J. Biol. Chem., 208 477 (1954). The minimum sum of FICS, which is the maximum synergy, was determined for various pairwise combinations. Alternatively, an average sum of the FICS is calculated, which is the average synergy. See Table S. These results indicate substantial synergy in the inhibition of virus spread. The smaller the number, the greater the synergy.

TABLE S

| Pairwise Combinations* | Average Synergy |
|---|---|
| 726 + ddI | 0.81 |
| 726 + AZT | 0.62 |
| 726 + 524 | 0.65 |
| 726 + 524 + AZT | |

524 is L-735,524. Other compounds are also defined in Table C above.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A method of inhibiting HIV reverse transcriptase comprising administering to a mammal a pharmaceutically acceptable carrier and an effective amount of a compound of Formula I:

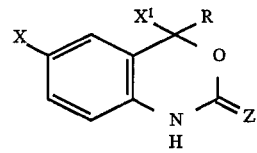

or pharmaceutically acceptable salt thereof, wherein:
X is halo,
$X^1$ is trihalomethyl, or pentahaloethyl;
Z is O;
R is:
(a) $C_{1-8}$ alkyl, unsubsdtuted or substituted with A, and A is halo, $C_{3-6}$ cycloalkyl, CN, hydroxy, $C_{1-4}$ alkoxy, $C_{2-4}$ alkynyl-$C_{1-4}$ alkoxy, aryloxy, $C_{1-4}$ alkylcarbonyl, nitro, di($C_{1-2}$ alkyl)amino, $C_{1-4}$ alkylamino- $C_{1-2}$ alkyl, heterocycle, or arylthio;
(b) $C_{2-4}$ alkenyl, unsubstituted or substituted with
  (i) A, or
  (ii) aryl, unsubstituted or substituted with A;
(c) $C_{2-5}$ alkynyl, unsubstituted or substituted with
  (i) A, or
  (ii) aryl, unsubstituted or substituted with A; or
(d) $C_{3-4}$ cycloalkyl, unsubstituted or substituted with
  (i) A, or
  (ii) aryl, unsubstituted or substituted with A,
or a compound of Formula II:

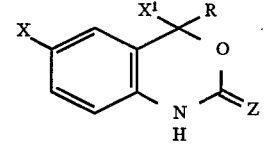

or pharmaceutically acceptable salt thereof, wherein:
X is halo;
$X^1$ is trihalomethyl; pentahaloethyl; $C_{2-5}$ alkyl;
$C_{2-5}$ alkynyl;
$C_{3-5}$ cycloalkyl; or aryl;
Z is O or S; and
R is:
(a) $C_{1-8}$ alkyl, unsubstituted or substituted with A, and A is halo, $C_{3-6}$ cycloalkyl, CN, hydroxy, $C_{1-4}$ alkoxy, $C_{2-4}$ alkynyl-$C_{1-4}$ alkoxy, aryloxy, $C_{1-4}$ alkylcarbonyl, nitro, di($C_{1-2}$ alkyl)amino, $C_{1-4}$ alkylamino-$C_{1-2}$ alkyl, heterocycle, or arylthio;
(b) $C_{2-4}$ alkenyl, unsubstituted or substituted with
  (i) A, or
  (ii) aryl, unsubstituted or substituted with A;
(c) $C_{2-5}$ alkynyl, unsubstituted or substituted with
  (i) A, or
  (ii) aryl, unsubstituted or substituted with A; or
(d) $C_{3-4}$ cycloalkyl, unsubstituted or substituted with
  (i) A, or
  (ii) aryl, unsubstituted or substituted with A.

2. A method of inhibiting HIV reverse transcriptase comprising administering to a mammal a pharmaceutically acceptable carrier and an effective amount of a compound selected from the group consisting of:

(−) 6-chloro-4-cyclopropylethynyl-4-trifluoromethyl-1,4-dihydro-2H-3,1-benzoxazin-2-one, (−) 6-chloro-4-phenylethynyl-4-trifluoromethyl-1,4-dihydro-2H-3,1-benzoxazin-2-one, (+/−) 6-chloro-4-

(2-cyanophenyl)ethynyl-4-(1,1,1-trifluoromethyl)-1,4-dihydro-2H-3,1-benzoxazin-2-one, (+/−)4-(1-chloro-1,1-difluoromethyl)-4-(2-phenylethynyl)-6-chloro-1,4-dihydro-2H-3,1-benzoxazin-2-one, or (+/−)4-(2-[dimethylaminomethyl]ethynyl)-4-trifluoromethyl-6-chloro-1,4-dihydro-2H-3,1-benzoxazin-2-one, or a pharmaceutically acceptable salt thereof.

3. A method of preventing infection of HIV, or of treating infection by HIV or of treating AIDS or ARC comprising administering to a mammal a pharmaceutically acceptable carder and an effective mount of a compound of Formula I:

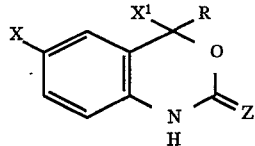   I or pharmaceutically acceptable salt thereof, wherein:

X is halo, $X^1$ is trihalomethyl, or pentahaloethyl;

Z is O;

R is:

(a) $C_{1-8}$ alkyl, unsubstituted or substituted with A, and A is halo, $C_{3-6}$ cycloalkyl, CN, hydroxy, $C_{1-4}$ alkoxy, $C_{2-4}$ alkynyl-$C_{1-4}$ alkoxy, aryloxy, $C_{1-4}$ alkylcarbonyl, nitro, di($C_{1-2}$ alkyl)amino, $C_{1-4}$ alkylamino- $C_{1-2}$ alkyl, heterocycle, or arylthio;

(b) $C_{2-4}$ alkenyl, unsubstituted or substituted with
(i) A, or
(ii) aryl, unsubstimted or substituted with A;

(c) $C_{2-5}$ alkynyl, unsubstituted or substituted with
(i) A, or
(ii) aryl, unsubstimted or substituted with A; or (d) $C_{3-4}$ cycloalkyl, unsubstituted or substituted with
(i) A, or
(ii) aryl, unsubstimted or substituted with A, or a compound of Formula II:

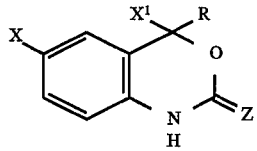   II or pharmaceutically acceptable salt thereof, wherein:

X is halo;

$X^1$ is trihalomethyl; pentahaloethyl; $C_{2-5}$ alkyl;

$C_{2-5}$ alkynyl;

$C_{3-5}$ cycloalkyl; or aryl;

Z is O or S;

R is:

(a) $C_{1-8}$ alkyl, unsubstimted or substituted with A, and A is halo, $C_{3-6}$ cycloalkyl, CN, hydroxy, $C_{1-4}$ alkoxy, $C_{2-4}$ alkynyl-$C_{1-4}$ alkoxy, aryloxy, $C_{1-4}$ alkylcarbonyl, nitro, di($C_{1-2}$ alkyl)amino, $C_{1-4}$ alkylamino-$C_{1-2}$ alkyl, heterocycle, or arylthio;

(b) $C_{2-4}$ alkenyl, unsubstimted or substituted with
(i) A, or
(ii) aryl, unsubstituted or substituted with A;

(c) $C_{2-5}$ alkynyl, unsubstituted or substituted with
i) A, or
(ii) aryl, unsubstituted or substituted with A; or (d) $C_{3-4}$ cycloalkyl, unsubstituted or substituted with
(i) A, or
(ii) aryl, unsubstituted or substituted with A.

4. A method of preventing infection of HIV, or of treating infection by HIV or of treating AIDS or ARC, comprising administering to a mammal a pharmaceutically acceptable carder and an effective amount of a compound selected from the group consisting of:

(−) 6-chloro-4-cyclopropylethynyl-4-trifluoromethyl-1,4-dihydro-2H-3,1-benzoxazin-2-one, (−) 6-chloro-4-phenylethynyl-4-trifluoromethyl-1,4-dihydro-2H-3,1-benzoxazin-2-one, (+/−) 6-chloro-4-(2-cyanophenyl)ethynyl-4-(1,1,1-trifluoromethyl)-1,4-dihydro-2H-3,1-benzoxazin-2-one, (+/−) 4-(1-chloro-1,1-difluoromethyl)-4-(2-phenylethynyl)-6-chloro-1,4-dihydro-2H-3,1-benzoxazin-2-one, or (+/−) 4-(2-[dimethylaminomethyl]ethynyl)-4-trifluoromethyl-6-chloro-1,4-dihydro-2H-3,1-benzoxazin-2-one, or a pharmaceutically acceptable salt thereof.

\* \* \* \* \*

UNITED STATES PATENT AND TRADEMARK OFFICE
CERTIFICATE OF CORRECTION

PATENT NO. : 5,663,169

DATED : 9/2/97

INVENTOR(S) : Steven D. Young, Linda S. Payne, Susan F. Britcher, Lekhanh O. Tran and William C. Lumma, Jr.

It is certified that error appears in the above-identified patent and that said Letters Patent is hereby corrected as shown below:

Column 32, Claim 1, line16, beginning with (a) C1-8 alkyl, please correct the word "unsubsdtuted" to read --unsubstituted--.

Column 33, Claim 3, line 13, beginning with carder, please correct the word "carder" to read --carrier-- and the word "mount" to read --amount--.

Column 33, Claim 3, line 34, beginning with (ii) aryl, please correct the word "unsubstimted" to read --unsubstituted--.

Column 33, Claim 3, line 38, beginning with (ii) aryl, please correct the word "unsubstimted" to read --unsubstituted--.

Column 33, Claim 3, line 41, beginning with (ii) aryl, please correct the word "unsubstimted" to read --unsubstituted--.

Column 34, Claim 3, line 15, beginning with (b) C2-4, please correct the word "unsubstimted" to read --unsubstituted--.

Column 34, Claim 4, line 29, beginning with carder, please correct the word "carder" to read --carrier--.

Signed and Sealed this

Ninth Day of December, 1997

*Attest:*

BRUCE LEHMAN

*Attesting Officer*   Commissioner of Patents and Trademarks